United States Patent [19]
Stosz et al.

[11] Patent Number: 5,418,156
[45] Date of Patent: May 23, 1995

[54] AGARASE ENZYME SYSTEM FROM ALTEROMONAS STRAIN 2-40

[75] Inventors: Sarah K. Stosz, Hyattsville; Ronald M. Weiner, Adelphi, both of Md.; Vernon E. Coyne, Rondebosch, South Africa

[73] Assignee: University of Maryland, College Park, Md.

[21] Appl. No.: 57,022

[22] Filed: May 5, 1993

Related U.S. Application Data

[63] Continuation of Ser. No. 684,742, Apr. 15, 1991, abandoned.

[51] Int. Cl.$^6$ ............................................. C12N 9/24
[52] U.S. Cl. .................................. 435/200; 435/195; 435/201; 435/69.1
[58] Field of Search ............... 435/195, 200, 201, 69.1

[56] References Cited

U.S. PATENT DOCUMENTS 4,503,035  3/1985  Pestka et al. .................. 424/85.4

OTHER PUBLICATIONS

Morrice et al. (1983) Eur J. Biochem. 135, 553–558.
Sofer et al. (1983) Bio Techniques Nov./Dec. 198–203.
Day et al. (1975) Can J. Microbiol. 21, 1512–1518.
Groleau et al. (1977) Can J. Microbiol 23, 672–679.
Agbo et al. (1979) J. Gen. Microbiol. 115, 355–368.
Andrykovitch et al (1988) Appl. Env. Microbiol. Apr. 1988.
Belas et al. (1988) Appl. Env. Microbiol. 54, 30–37.
Kendall et al (1984) Gene 29, 315–321.
Aoki et al., Eur. J. Biochem. vol. 187, 1990, pp. 461–465.
Yamaura et al., Agric. Biol. Chem., vol. 55(10) 1991, pp. 2531–2536.
Aoki et al., Nippon Suisan Gakkaishi, vol. 56(5), 1990, pp. 825–830.
Duckworth et al., Chemical Abstracts, vol. 71(9), 1969, #36039z.
Duckworth et al., Chemical Abstracts, vol. 71(15), 1969, #67552r.
Van der Meulen et al., Chemical Abstracts, vol. 82(13), 1974, #82858r.
Van der Meulen et al., Chemical Abstracts, vol. 84(15) 1975, #101298t.
Young et al., Chemical Abstracts, vol. 83(1), 1975, #3490j.
Young et al., Carb. Res., vol. 66, 1978, pp. 207–212.
Malmquist, Carb. Res., vol. 62, 1978, pp. 337–348.
Malmquist, Biochim. Biophys. Acta., vol. 537, pp. 31–43 (1978).
M. Morrice et al., Eur. J. Biochem., vol. 135, 1983, pp. 553–558.
M. Morrice et al., Eur. J. Biochem., vol. 137, 1983, pp. 149–154.
M. Morrice et al., Chemical Abstracts, vol. 102(3), 1985, #20179t.
Kendall et al., Chemical Abstracts, vol. 102(1), 1985, #135000.
Fukasawa et al., Agri. Biol. Chem., vol. 51(1), 1987, pp. 269–270.
Bibb et al., J. Gen. Micro., vol. 133, 1987, pp. 2089–2096.
Sampietro et al., Biochemica et Biophysica Acta, vol. 244, 1971, pp. 65–76.
Kono et al., Chemical Abstract, vol. 111(9), 1989, #73534x.
D. Groleau, Enzymatic hydrolysis of agar: purification and characterization of $\beta$-neoagarotetraose hydrolase from Pseudomonas atlantica, Feb. 16, 1977 23:672–679.
Agbo, The Isolation and Characterization of Agarolytic (List continued on next page.)

Primary Examiner—Keith Baker
Attorney, Agent, or Firm—Burns, Doane, Swecker & Mathis

[57] ABSTRACT

This invention relates to an agarase enzyme system purified from bacterial strain 2-40, which has a high level of activity for the depolymerization of complex polysaccharides, including agar and agarose. Further, the invention relates to methods of purifying, defining, characterizing and assaying the agarase enzyme system and the encoding gene(s). Finally, the invention relates to methods of using the purified agarase enzyme system.

7 Claims, 4 Drawing Sheets

OTHER PUBLICATIONS

Bacteria from a Lowland River Journal of Gen. Microbiology (1979) 115. 355–368.

Day, Enzymatic hydrolysis of agar: purification and characterization of neoagarobiose hydrolase and p-nitrophenyl α-galactoside hydrolase, (1975), Can. J. Micro–biol 1512–1518.

Hodgson et al., A Chromosomal Locus Controlling Extracellular Agarase Production by *Streptomyces coelicolor* A3(2), and its Inactivation by Chromosomal Integration of Plasmid SCP1, Jour. of Gen. Microbiology (1981) 124, 339–348.

Sampietro et al., Characterization of the Agarolytic system of Agarbacterium pastinator, Biochim. Biophys. Acta, 244 (1971) 65–76.

Duckworth et al., Biochem, J. (1969) 113, 693, The Specificity of an Agarase from a Cytophaga Species.

Duckworth et al., Biochem, J. (1969) 113, 139, An Extracellular Agarase from a Cytophaga Species.

Duckworth et al., Biochem, J. (1969) 113, 687, The Action of a Bacterial Agarase on Agarose, Porphyran and Alkali-treated Porphyran.

Garnder et al, Jour. of Bacteriology (1987), pp. 4581–4588, Purification and Characterization of an Ex-o–β–1, 4–Glucanase from *Ruminococcus flavefaciens* Fd–1.

Morriece et al., J. Biochem 137, 149–154 (1983), Agarases I and II from *Pseudomonas atlantica*.

Duckworth et al., Jour. of Chromoatography, 49 (1970) 482–487, Thin–Layer Chromatographic Analysis of Enzymic Hydrolysates of Agar.

Yaphe, Can. J. Microbiol. 3 (1957) The Use of Agarase from *Pseudomonas Atlantica* in the Identification of Agar in Marine Algae.

Belas et al., Applied and Eviron. Microbiol. (1988) pp. 30–37, Cloning and Gene Replacement Mutagenesis of a *Pseudomonas atlantica* Agarase Gene.

Andrykovitch, Amer. Soc. for Microbio. (1988) Isolation of a New Polysaccharide–Digesting Bacterium from a Salt Marsh.

Thesis by Irene Marx, Isolation and Characterization of an Agar–Degrading Bacterium (George Mason University (1986).

Kendall, Cloning and expression of an extracellular–agarase gene from *Streptomyces coelicolor* A3(2) in *Streptomyces lividans* 66. (1984) Elsevier Sciene Publisher, p. 315.

AGARASE ENZYME SYSTEM FROM ALTEROMONAS STRAIN 2-40

This invention was made with Government support under Contract N00014-86-K-0696 awarded by the Department of the Navy. The Government has certain rights in the invention.

This application is a continuation of application Ser. No. 07/684,742, filed Apr. 15, 1991, now abandoned.

BACKGROUND OF THE INVENTION

Field of the Invention

This invention relates to an agarase enzyme system purified from bacterial strain 2-40, which has a high level of activity for the depolymerization of complex polysaccharides, including agar and agarose. Further, the invention relates to methods of purifying, defining, characterizing and assaying the agarase enzyme system and the encoding gene(s). Finally, the invention relates to methods of using the purified agarase enzyme system.

Discussion of the Prior Art

Estuarine salt marshes are highly productive systems in which microorganisms have an important role in decomposition, nutrient cycling, and production of particulate matter. The marsh grass, Spartina alterniflora, is one of the principal sources of carbon and energy for the microbial community. The gram negative bacterium, designated strain 2-40, has been isolated from a Chesapeake Bay salt marsh in Matthews County, Va., where it was growing periphytically on the marsh grass *S. alterniflora*.

The culture of strain 2-40 was initially obtained from 1% peptone-half-strength-seawater agar plates which had been pressed into partially decomposed *S. alternifiora* at the Chesapeake Bay salt marsh, as reported by Andrykovitch and Marx in *Appl. Environ. Microbiol.* 54:3-4 (1988). The bacterial strain 2-40, as initially isolated, has been deposited with the American Type Culture Collection (12301 Parklawn Drive, Rockville, Md.) as ATCC No. 43961. Strain 2-40, presumptively identified as a member of the genus Alteromonas, is an aerobic, pleomorphic rod shaped marine bacterium which is motile by means of a single polar flagellum. The organism can tolerate wide temperature, pH and salinity ranges. Strain 2-40 produces a large number of hydrolytic enzymes which degrade a variety of complex polysaccharides including alginic acid, xylan, and agar. It also produces a chitinase, tyrosinase and enzymes which can degrade lipids. Further, strain 2-40 also produces an exopolymer.

Since the first description of an agarase in 1902 by Gran, [Stanier, *J. Bacteriol.* 42:527-559 (1942)] relatively few genera of bacteria have been isolated which degrade agar. Most strains of agar-degrading bacteria are marine and require a high salt concentration [Yaphe, *Can. J. Microbiol.* 3:987 (1957); Corpe et al., *Can. J. Microbiol.* 18:1483 (1972); Christensen, *Can. J. Microbiol.* 23:1599 (1977); Quatrano et al., *Appl. Environ. Microbiol.* 36:979 (1978)]. However, agarolytic bacteria have also been isolated from other sources, including soil [*Streptomyces coelicolor* by Stanier (1942); *Agarbacterium pastinator* by Sampietro et al., *Biochem. Biophys. Acta* 244:65 (1971)]; from a blood agar plate in a hospital [an *Agarbacterium* by Swatz et al., *J. Bacteriol.* 77:403 (1959)], and from rivers [*Cytophaga flevensis* by van der Meulen, *Antonie van Leeuwenhoek* 41:431 (1975)]. Several unidentified species of agarolytic bacteria have also been isolated from rivers by Agbo et al., *J. Gen. Microbiol.* 115:355 (1979).

Agar is a complex polysaccharide derived from the agarophytes of the Rhodophyteaa (red seaweeds). In the United States, it is mainly extracted from *Gelidium cartilagineum*, while in South Africa and Australia it is obtained from *Gracilaria confervoides*, in New Zealand from Pterocladia species, in the U.S.S.R. from *Ahnfeldtia plicata*, and in Japan from *Gelidium amansii*. Each of the agars differ in gel strength due to varying amounts of agarose and agaropectin, the two main components of agar. The agar gel comprises a matrix of double-helical polymer chains held together by hydrogen bonds.

Agarose is the gelatinous, non-branched portion of agar. The agarose is assumed to be neutral, but it can in fact contain small amounts of sulphate esters, imparting to the agar a weak negative charge. Agarose is a repeating sequence of (1-4)-linked 3,6 anhydro-$\alpha$-L-galactose and (1-3)-linked $\beta$-D-galactose. [Roehrig, *Carbohydrate Biochemistry and Metabolism*, Avi Publishing Co. 1984]. Agaropectin is the ionic, nongelatinous portion of agar. Its galactoside units may be methylated or contain sulfate and pyruvate in varying amounts [Araki et al., *Bull. Chem. Soc. Jap.* 29:339 (1956)] as well as D-glucuronic acid (Roehrig, 1984).

The breakdown of the complex agar polysaccharide to simple sugars is exemplified by a Pseudomonas atlantica agarase system at a paradigm which is a three enzyme agarase system proposed to operate in the following manner. See, FIG. 1. The first enzyme is a $\beta$-agarase, designated $\beta$-agarase I. $\beta$-agarase I is an endoenzyme which acts on the -1,4 linkages between D-galactose and 3,6-anhydro-L-galactose, resulting in a neoagarotetraose tetramer end product. $\beta$-agarase I can also act on neoagarooctaose and neoagarohexaose. The -agarase I enzyme is extracellular.

Figure 1:
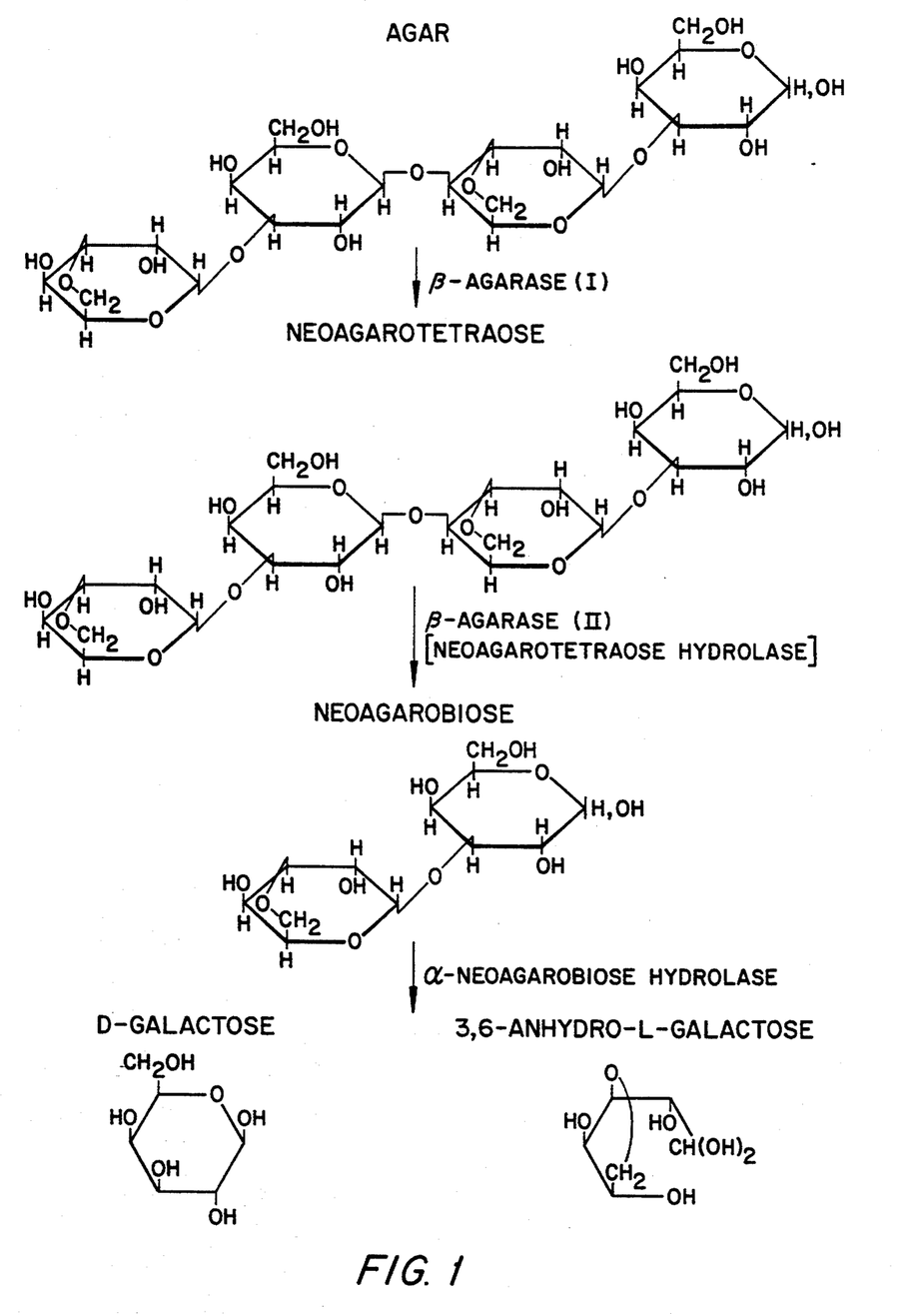
FIG. 1 is a diagramatic representation showing a 3-step chemical degradation of agar by agarases to the final simple sugar products.

The second enzyme, referred to as either $\beta$-agarase II or neoagarotetaose hydrolase is also a -agarase. $\beta$-agarase II cleaves the central -1,4 linkage of the tetramer produced by the $\beta$-agarase I to yield a neoagarobiose dimer. Mild acid hydrolysis of agar can result in an agarobiose dimer rather than neoagarobiose. The second agarase enzyme also has residual exoenzymatic activity on the large agar polymer. The $\beta$-agarase II enzyme is cell wall associated.

The final enzyme in the agarase system is an $\alpha$-agarase. The $\alpha$-agarase enzyme cleaves the $\alpha$ linkage of neoagarobiose to yield D-galactose and 3,6-anhydro-L-galactose. The cellular location of this neoagarobiose hydrolase is not clear.

Visible changes caused by cleavage of the agar molecule range from the softening of the surface of the gel to the formation of craters and eventual complete liquification. Other complex polysaccharides that are often degraded by saccharolytic bacteria are alginic acid, carrageenan, inulin, araban, pectin, dextran, chitin, laminaran, starch, glycogen, pullulan, cellulose, fucoidan, and xylan.

Most presently described agarolytic bacteria are considered to possess only a $\beta$-agarase system. However, enzymatic pathways involving enzymes which initially attack the agar polymer at its linkages may also exist. The bacterial $\beta$-agarase enzyme is known to be produced by bacteria from several taxonomically diverse genera, including Cytophaga, Streptomyces, and Pseudomonas. However, biochemical and genetic studies have shown that there appears to be diversity among β-agarase proteins and genes, even though the enzymes are functionally similar in the catalysis of the agar backbone. The enzymes are of widely varying sizes, for example, *C. flevensis* is about 26,000 daltons, *S. coelicolor* is about 28,000 daltons, and *P. atlantica* is about 49,000 daltons. Of the three principal genera characterized as agar-digesting bacteria, most research to date has focused on the agarolytic properties of the marine bacterium, *Pseudomonas atlantica*. Belas et al., *Appl. Environ. Microbiol.* 54:30 (1988); Belas, *J. Bacteriol.* 171:602 (1989).

Classical methods of bacterial classification are based on morphological, physiological, and biochemical characteristics. Properties such as colony and cell morphology, staining behavior, sugar metabolism, enzyme production, and growth in the presence of inhibitory compounds determine the assignment of strains to particular groups. Recently, studies of genetic relatedness, serology, and chemotaxonomy have gained in accessibility and their application has become more widespread for bacterial identification purposes.

Most genetic analysis is based on an investigation of similarities between the deoxyribonucleic acid (DNA) or the ribonucleic acid (RNA) of different organisms. Methods commonly used include DNA/DNA hybridization, DNA/mRNA hybridization, oligonucleotide probing, and also protein sequencing. However, the richest source of information in the DNA macromolecule is the nucleotide sequences of complete bacterial genomes. The two features of DNA most widely used for the direct analysis of the chromosomal DNA are the overall base composition (mol % guanine+cytosine content) and comparative base sequence similarities obtained by in vitro DNA—DNA molecular hybridization.

The ratio of adenine (A) plus thymine (T) to guanine (G) plus cytosine (C) or the mol % guanine plus cytosine (% G+C=100 (G+C)/(A+T+G+C)) of prokaryotic DNA varies between different taxa within the range of 23% to 78% G+C. Dissimilarity in % G+C of DNA between two strains establishes that they are different. In general, bacteria with more than 5% difference in % G+C would not be classified in the same species, and those showing differences over 10% would not be assigned to the same genus. Homology studies make use of the renaturation property of DNA, so that the DNA from closely related strains will almost completely reanneal, while sparse duplex formation implies distant genetic relatedness.

To detect differences or similarities between bacteria, serological techniques based on the antigenicity of cell surface components are used. Also, antisera against purified enzymes are used to compare homologous proteins from different bacteria. Chemotaxonomy is used to classify bacteria on the basis of their chemical composition. The cell components that are most often analyzed are the cell wall, lipids, proteins, and redox carriers such as quinones and cytochromes.

While DNA is the source of all taxonomic information, its translation into sequences of amino acids yields a product that is easily manipulated. Comparative analyses of specific homologous proteins provide accurate means of establishing relationships between bacteria. Changes in the amino acid sequence of specific proteins can reflect evolutionary divergence between organisms.

Comparison of isolated strain 2-40 of the present invention with organisms having similar morphological and physiological traits suggested that it is not a member of any known species. Its G+C content (45.66 mole % G+C, as determined by the American Type Culture Collection, Rockville, Md.) was within the range of G+C content of only Oceanospirillum, Vibrio, and Alteromonas spp. [see, Krieg et al., Bergey's Manual of Systematic Bacteriology (1984)]. Unlike strain 2-40, Oceanospirillum spp. do not metabolize sugars and have bipolar flagellation and permanently helical cells. Furthermore, by comparison, Vibrio spp. differ in the fermentation of sugars and have sheathed flagella.

Strain 2-40 cannot be identified as an existing species of Alteromonas, but it could be classified within this heterogeneous and complex genus, which has been described in the Bergey's Manual as follows:

Straight or curved rods, 0.7–1.5 m in diameter and 1.8–3.0 m in length. Do not accumulate poly-β-hydroxybutyrate (PHB) as an intracellular reserve product. Microcysts or endospores are not formed. Gram-negative. Motile by means of single polar flagella. Chemoorganotrophs-capable of respiratory but not fermentative metabolism. Molecular oxygen is a universal electron receptor, do not denitrify . . . require a seawater base for growth . . . grow at 20° C. Common inhabitants of coastal waters . . . The mol % G+C content of the DNA is 38–50 mol % ($T_m$, Bd).

Moreover, strain 2-40 has been found to have the same G+C content as Alteromonas, strain LST, a non-polysaccharide digesting, melanin producing marine bacterium recently characterized by Weiner et al. [*Appl. Environ. Microbiol.* 49:83 (1985)]. However, no DNA homology has been reported between the two organisms.

Pseudomonas atlantica agarase is commercially available and provides a basis for comparison of specific activity in the novel enzyme of the present invention. However, the commercially prepared agarase is of low activity. Thus, there remains a long-felt need in the art for the isolation of an agarase gene and the expression of an agarase enzyme system having a high level of activity for the depolymerization of polysaccharides, in particular for the depolymerization of agar to simple sugar products. The agarase enzyme system of strain 2-40, because of its stability and high level of activity over a broad range of temperatures and pH conditions, would be of particular economic importance in the production of simple sugars, including neoagarobiose, neoagarotetraose and neoagarohexaose. Commercially available sugar sources from red algae could provide economically profitable feed additives, or human food products. Furthermore, a purified agarase from the enzyme system of the 2-40 strain could provide an important biotechnological tool. It could effectively degrade agarose to oligosaccharides, thereby providing the liquification of agar and agarose gels and the defouling of fermentors and bioreactors. Moreover, the purified enzyme could effectively control red algae bloom contaminations, prevent the biofouling of submerged marine surfaces or pipes by contaminating complex polysaccharide layers, or treat such biofouled surfaces after contamination.

SUMMARY OF THE INVENTION

Accordingly, it is a primary object of this invention to provide a novel enzyme system which is useful for a number of applications.

It is a particular object of this invention to provide a purified novel microorganism which can produce a novel enzyme system which is useful for effecting the depolymerization of complex polysaccharides.

It is a more particular object of this invention to provide a purified enzymatic product having a high level of agarase activity.

It is also a particular object of this invention to provide genetically engineered constructs containing the genes coding for said enzyme system.

According to a further object of this invention there is provided a method of purifying the novel microorganism which can produce the novel enzyme system which is useful for effecting the depolymerization of complex polysaccharides.

It is a particular object of this invention to provide a method of purifying the purified enzymatic product having a high level of agarase activity.

Further, it is an additional object of this invention to provide a method of purification of foreign proteins comprising a DNA fusion of the gene of the protein of interest to the gene for the agarase.

According to an additional object of this invention there are provided the depolymerized products of complex polysaccharides.

It is another object of this invention to provide the depolymerized products of complex agar polysaccharides.

According to a further object of this invention there are provided assay methods to define the novel enzyme system having a high degree of agarase activity.

It is also an object of this invention to provide assay methods to define other novel enzyme systems.

It is an object of the present invention to provide an agarase enzyme system isolated from the purified, isolated bacterial strain 2-40 as well as a biologically pure culture of the marine bacterial strain 2-40 which produces an agarase which effectively depolymerizes complex polysaccharides, is aerobic, rod shaped, and can grow on minial media having agar or agarose as the sole carbon source along with the structural gene coding for the enzyme system.

A further object of the present invention is to disclose a novel microorganism transformed with a vector coding for an agarase enzyme system.

Another object is to describe a recombinant DNA construct comprising a 2-40 DNA insert having approximately 8 kb inserted into a pEcoR252.

The invention is also directed to a process for purifying the novel agarase enzyme system comprising:
a) amplifying the cells of strain 2-40 on minimal media supplemented with an agar or agarase carbon source;
b) harvesting the cell supernatant;
c) selecting the cell supernatant for molecular weight fragments greater than 30,000;
d) electrophoretically size fractionating the selected portion of the cell supernatant on a separation polyacrylamide gel;
e) blotting the completed gel of step (d) in direct contact with an overlay second polyacrylamide gel;
f) visualizing the agarase activity on the overlay gel by means of an iodine staining assy;
g) excising the agarase active regions from a third polyacrylamide gel used to electrophoretically fractionate the 2-40 cell supernatant by the manner of steps (b) through (d); and
h) electroeluting the purified agarase of high specific activity from the excised gel bands of step (g).

It is another object of the present invention to provide a recombinant plasmid for the expression of the agarase enzyme system, comprising an 8kb DNA insert coding for the 2-40 agarase enzyme system ligated to the vector pEcoR252.

Another object is to provide a recombinant DNA construct comprising a promoter, a signal sequence and a structural gene.

Yet another object of the present invention is to disclose a method for detecting foreign genes in a host material, said method comprising inserting a recombinant DNA construct into a foreign vector as a reporter gene wherein cells which express agarase activity are identified.

According to a further object of the present invention is a method for the purification of a foreign protein, said method comprising:
a) fusing the gene of the foreign protein to a cloned agarase gene generating a translational fusion vector;
b) transforming said translational fusion vector into a host organism for propagation;
c) extracting proteins from said organism;
d) allowing said extracted proteins to interact with agarose; and
e) selecting for said fusion protein based on its binding to the agarose.

A still further object of the present invention is to provide a method for maximizing the yield of an agarase enzyme comprising:
a) amplifying the cells of strain 2-40 on minimal media supplemented with an agar or agarose carbon source for a sufficient time, temperature and under aeration conditions to effect optimal expression of the agarase.

The present invention also discloses vectors useful in biotechnology which will be engineered to carry the agarase gene. Those successful recipient cells will then be differentiated by their typical agarase colonial morphology.

It is also the object of this invention to provide a selective reporter gene strategy based on the agarase operon in which a cloning cassette with polylinker flanking is constructed into which foreign genes may be inserted. Recombinants (clones) will not grow on replica plates containing only basal agarose medium.

It is a final object of this invention to provide a method of defouling substrates which have become biofouled upon exposure to complex polysaccharide marine by-products.

DESCRIPTION OF THE PREFERRED EMBODIMENTS OF THE INVENTION

This invention embodies the fermentation and purification of a novel agarase enzyme system from bacterial strain 2-40, the cloning of the agarase enzyme gene(s) into an *Escherichia coli* expression system so that agarose is utilized as the sole carbon source, the production of an agarase enzyme system having a high level of specific activity for the depolymerization of complex polysaccharide matrices, and the characterization of the agarase enzyme system by means of novel assay methods.

The novel agarase enzyme system may be purified from the bacterial strain 2-40, which was initially isolated from partially decomposed salt-marsh grass, Spartina alterniflora, as reported by Andrykovitch and Marx in Appl. Environ. Microbiol. 54:3-4 (1988) (ATCC No. 43961). Strain 2-40, presumptively identified as a member of the genus Alteromonas, is an aerobic, pleomorphic rod shaped marine bacterium which is motile by means of a single, unsheathed polar flagellum. Cells can average about 0.5 $\mu$m in width and 1.5 to 3.0 $\mu$m in length. In stressed cultures, filaments and coils of up to 20 $\mu$m can be formed. Spheroplasts, can appear in old cultures, and subsequently autolyse.

Figure 3:
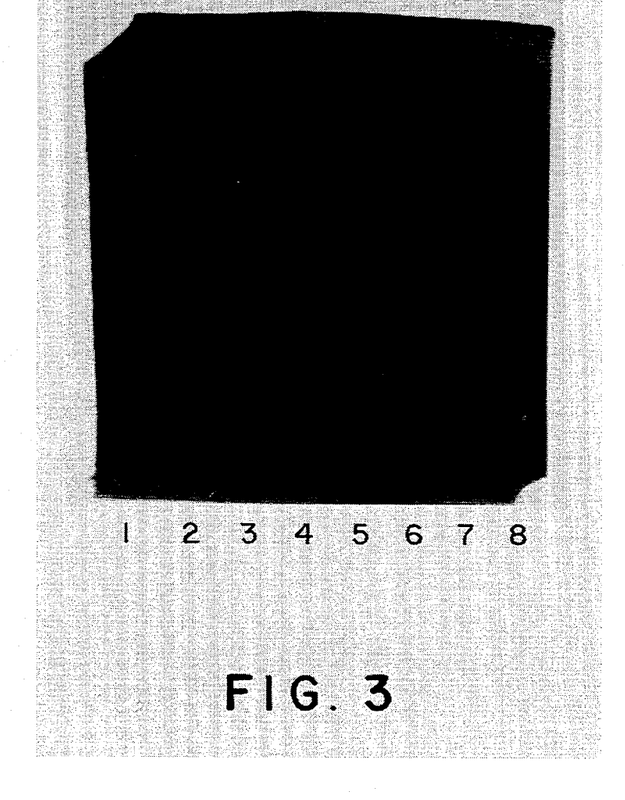
FIG. 3 is a photographic representation of the electrophoretically separated proteins from strain 2-40 cultured on the 2-40 minimal agarase induction media representing the proteins expressed by the whole cell, the cytosolic portion, the inner membrane, the outer membrane, and the media supernatant at 18 or 30 hour timepoints.
Figure 4:
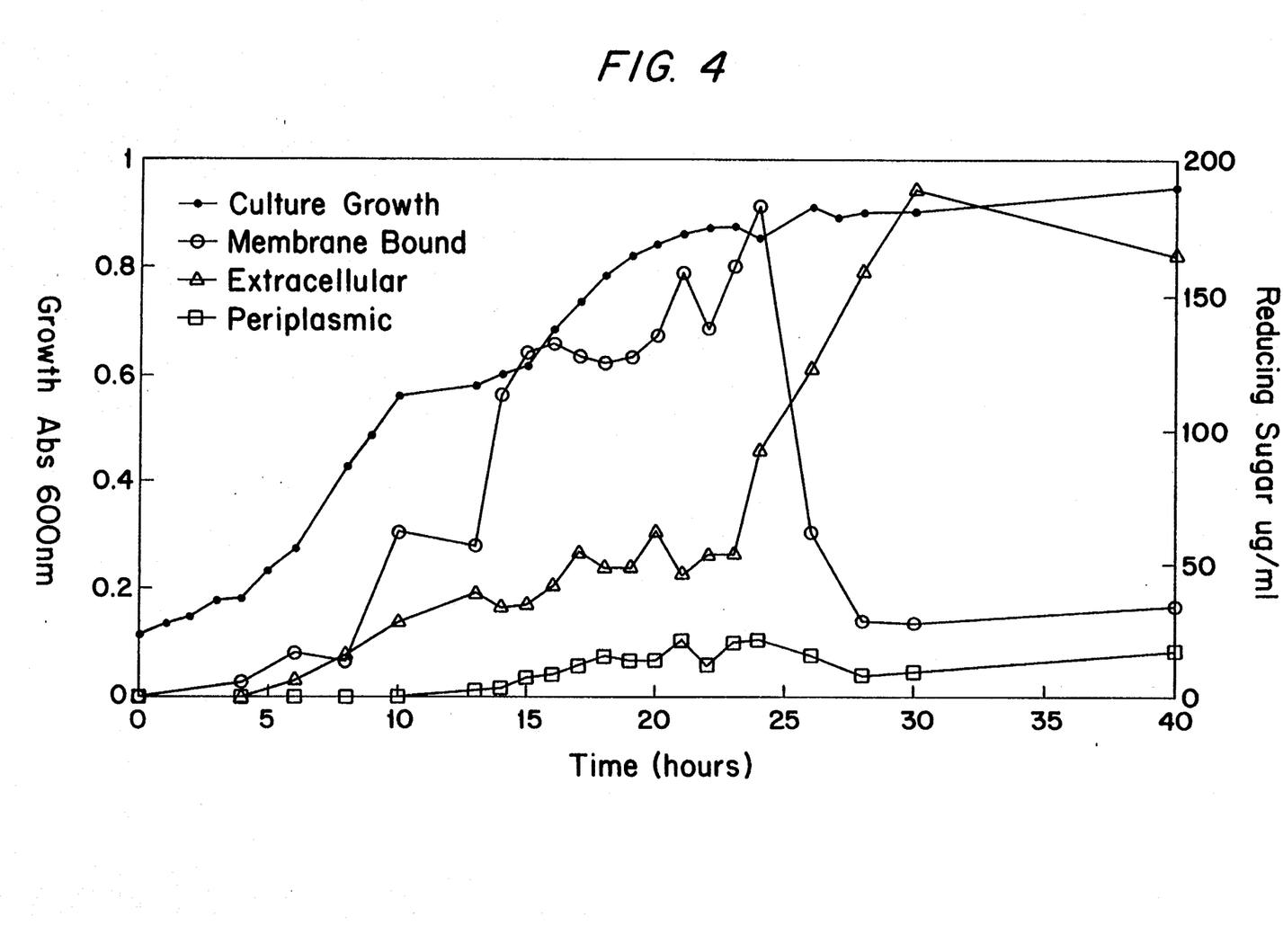
FIG. 4 is a graphic representation of the optimal growth curve of bacterial strain 2-40 on the 2-40 minimal agarase induction media.

Growth and standard biochemical tests can be carried out by making appropriate additions to suitable growth media. Although strain 2-40 can grow well in the mineral medium of Niven [*J. Gen. Microbiol.* 98:95 (1977)], growth is more rapid with organic nitrogen than with $NH_4$ as the nitrogen source, in particular, growth can be optimally achieved in Difco marine broth 2216 (Difco Laboratories, Inc.). Optimal expression of the agarase enzyme is achieved when bacterial strain 2-40 is grown on the 2-40 minimal agarase induction media as shown in FIG. 3 and FIG. 4. Tyrosine enhances production of melanin. Kelly et al., *FEMS, Microbiology Letters* (1990). An ethanol-insoluble, anthronepositive polymer accumulates when glucose is the carbon and energy source.

Sugar oxidation-fermentation tests can be performed by a modification of the Leifson method for marine microbes [*J. Bacteriol.* 85:1183 (1963)]. The 2-40 organism is catalase and preoxidase positive and non-fermentative. Growth requires sea salts and carbohydrate additives. The temperature range for growth was 5 to 40° C., and the most rapid growth occurred at 37° C. The pH can range from 5 to 9.2, while the optimum pH is 7.5.

Strain 2-40 is capable of lipolysis (with Tween 20 and Tween 80) and caused alpha-hemolysis of sheep and human erythrocytes. Acid is produced when the polysaccharide carbon source is arabinose, cellobiose, dulcitol, fructose, galactose, glucose, galacturonic acid, glucuronic acid, maltose, mannose, ribose, salicin, sorbose, sucrose, or xylose.

To assess the polysaccharide digestion, cultures may be grown in minimal medium supplemented with polysaccharide as the carbon and energy source. Log-phase culture supernatant would be incubated with a buffered polysaccharide solution so that hydrolysis of the polysaccharide can be determined. In particular, by measuring the released reducing sugars, i.e., colorimetrically with a dinitrosalicylic acid reagent using glucose as the standard, or to achieve more sensitivity by a ferric cyanide reducing sugar assay in conjunction with thin layer chromotography, or most particularly by an iodine staining assay developed specifically to indicate agarase activity. Further, chitin breakdown may be measured by N-acetylglucosamine release. The 2-40 agarase enzyme system is highly effective for the depolymerization of certain complex polysaccharides, i.e., agar, agarose, alginic acid, carboxymethylcellulose, chitin, glycogen, laminarin, pullulan, sodium polygalacturonate, starch, and xylan, in particular agar and agarose. However, the 2-40 agarase enzyme system selectively does not digest carrageenan, cellulose, dextran, inulin, pectin, and polygalacturonic acid.

Once a host strain has been identified, numerous techniques may be employed to identify the coding sequence for the agarase enzyme system. The gene may be present on a chromosome or plasmid. The genome may be fragmented, particularly with restriction endonuclease, where one or more endonucleases may be employed to provide fragments ranging in size from less than 1 kb to about 50 kb. These fragments may be cloned on appropriate vectors in a convenient bacterium, e.g., Bacillus, Escherichia Salmonella, or the like, Neurospora, or yeast; however, numerous other bacterium would be suitable and are known by those of ordinary skill in the art. The resulting transformants may be screened for enzyme activity, particularly for agarase activity, where the host organism provides a negative background.

Once one or more clones have been identified as having agarase activity, the extrachromosomal elements containing the desired DNA fragment, plasmids, cosmids or viruses may be isolated by conventional techniques, such as lysis of the host, precipitation of the DNA, and separation of the vector DNA, plasmid or virus DNA, from the chromosomal DNA. The extrachromosomal elements may then be cleaved by endonuclease restriction and the desired fragments isolated by various techniques for separation and identification of fragments of different sizes, e.g., electrophoresis, density gradient centrifugation, or the like.

Depending on the size of the identified fragment, it will usually be further manipulated to reduce its size to more closely approximate the size of the gene and its flanking regulatory sequences. Partial cleavage with different restriction enzymes in different reaction mixtures may be employed, followed by cloning of the fragments to determine which of the fragments still retain the ability to provide agarase activity.

Alternatively, the enzyme system may be isolated and partially sequenced. Based on the amino acid sequence, probes can be prepared which may then be used to identify those fragments having the gene(s). By combining this approach with the restriction enzyme cleavage, fragments can be cloned and screened for the presence of the desired gene(s). In addition, one may use exonucleases, such as Bal31 to remove nucleotides from one or both ends of the fragment to further reduce the number of superfluous nucleotides.

Alternatively, the gene(s) may be cloned in an appropriate host from which the messenger RNA (mRNA) can identified by screening, i.e., by oligonucleotide probing methods. The mRNA may also be identified in an appropriate in vitro or in vivo translation system, e.g., Xenopus oocytes or reticulolysate, or the like. The isolated messenger may then be used for preparing cDNA using conventional techniques involving a reverse transcriptase and formation of the complementary chain with a DNA polymerase. In this instance, the resulting structural gene lacks the regulatory regions associated with transcription.

The gene(s) coding for agarase activity may be modified in a variety of ways, truncating either or both of the 5'- or 3'-termini, extending the 5'- or 3'-termini with additional nucleotides, or the like. Combinations of nucleotide substitution, truncation and extension may be employed. Thus, the gene(s) may be manipulated in a variety of ways to change the characteristic of the enzyme, to provide convenience in manipulation of the plasmids, or the like.

The DNA sequence containing the structural gene(s) expressing the agarase enzyme system may be joined to a wide variety of other DNA sequences for introduction into an appropriate host cell. The companion sequence will depend upon the nature of the host, the manner of introduction of the DNA sequence into the host, and whether episomal maintenance or integration is desired. May be joined to a variety of expression vectors such as lac promoter to boost activity.

For prokaryotic hosts, a wide variety of vectors exist which may be used for introduction by transformation, conjugation, transduction or transfection of the DNA sequence into a prokaryotic host. DNA sequences include a wide variety of plasmids, such as pBR322, pUC19, pMB9, pEcoR252 and the like; cosmids, M13 such as pVK100; or virus, such as phage, p22, and the like.

For eukaryotic hosts, a wide variety of techniques may be employed for DNA introduction into the host, such as transformation with Ca++-precipitated DNA, involving a non-replicating DNA sequence, a plasmid or a minichromosome, transformation, microinjection with a micropipette, electroporation, polyethylene glycol (PEG) mediated transformation of protoplasts, or gene gun or particle bombardment techniques. Whether the DNA may be replicated as an episomal element, or whether the DNA may be integrated into the host genome and the structural gene expressed in the host, will be determined by the presence of a competent replication system in the DNA construct. Episomal elements may be employed, such as tumor inducing plasmids, or fragments thereof, or viruses, including phages, or fragments thereof, which are not lethal to the host, and where the structural gene is present in such episomal elements in a manner allowing for expression of the structural gene(s). Of particular interest are fragments having the replication function and lacking other functions such as oncogenesis, virulence, and the like.

To introduce isolated genes or groups of genes into the genome of bacterial cells an efficient host/gene vector system is necessary. The foreign genes should be expressed in the transformed prokaryotic cells and stably transmitted, somatically or sexually to a second generation of cells produced. The vector should be capable of introducing, maintaining, and expressing a gene from a variety of sources in the host cells. Additionally, it should be possible to introduce the vector into a variety of hosts, and at a site permitting effective gene expression. Moreover, to be effective, the selected gene(s) must be passed on to progeny by normal reproduction.

The fragments obtained from purified 2-40 strain may be cloned employing an appropriate cloning vector. Cloning can be carried out in an appropriate unicellular microorganism, e.g., a bacterium, such as Escherichia, Bacillus, Salmonella or the like. In particular, one may use a phage, where partial or complete digestion provides fragments having about the desired size. For example, the phage lambda may be partially digested with an appropriate restriction enzyme and ligated to fragments resulting from either partial or complete digestion of a plasmid, chromosome, or fragment thereof. Packaging will insure that only fragments of the desired size will be inserted and transduced into the host organism.

The host organism may be selected for non-agarase activity. The recipient strains may be modified to provide for appropriate genetic traits which allow for selection of transductants. In microorganisms, the transductants may be used for conjugation to other microorganisms, using a mobilizing plasmid as required. Various techniques may be used for further reducing the size of the fragment containing the structural gene for the agarase activity. For example, the plasmid vector may be isolated, cleaved with a variety of restriction endonuclease, e.g., EcoRI, BamHI, Bgl II, and the like, and the resulting fragments cloned in an appropriate vector, the plasmid vector previously used, for instance, would be particularly suitable. Instead of a plasmid vector, a variety of cloning vectors are available in a number of suitable sizes.

Of particular interest is a partial Sau 3A digestion fragment from strain 2-40, containing the gene(s) coding for the agarase enzyme system. The 8 kb fragment is of particular interest when inserted into the suicide vector pEcoR252, to introduce the construct p5-2.

The agarase enzyme system may be expressed by any convenient source, either prokaryotic or eukaryotic, including bacteria, yeast, filamentous fungus, plant cells, and the like. Where secretion is not obtained, the enzyme may be isolated by lysing the cells and isolating the enzyme. Useful ways include chromatography, electrophoresis, affinity chromatography, and the like. The expression cassette of the present invention is of particular interest when expressed from prokaryotic host cells, more particularly from *E. coli* HB101.

The DNA sequence encoding for the agarase activity may be used in a variety of ways. Once the molecular basis of the agarase enzyme system is known, the method applied in the present invention for the fermentation, purification, identification and characterization of the enzyme system could be applied to other organisms. The DNA sequence may be used as a probe. Fusion proteins could be formed with the agarase gene(s) in an expression system, thereby utilizing the unique characteristics of the agarase enzyme system to identify and purify the fused gene of interest. Antibodies could be made to the agarase proteins which enable rapid identification or detection or purification of these enzymes or those cross-reacting enzymes from other organisms. Also saturation or site-directed mutagenesis could be performed on an agarase gene to select for mutants expressing greater levels of agarase activity stability, as well as the depolymerization of other complex polysaccharides. In the alternative, the DNA sequence may be used for integration by recombination into a host to provide agarase activity in the host.

With prokaryotic cells, the structural gene as part of a construct may be introduced into the host cell by calcium chloride transformation, transduction, conjugation, electroporation, or gene gun techniques. Where the structural gene has been obtained from a source having regulatory signals which are not recognized by the prokaryotic host, it may be necessary to introduce the appropriate regulatory signals for expression. Where a virus or plasmid, e.g., tumor inducing plasmid, is employed and has been mapped, a restriction site can be chosen which is downstream from a promoter into which the structural gene may be inserted at the appropriate distance from the promoter. Where the DNA sequences do not provide an appropriate restriction site, one can digest for various times with an exonuclease, such as Bal31 and insert a synthetic restriction endonuclease site (linker).

Various constructs can be prepared providing for expression in prokaryotic cells. To provide for transcription, a variety of transcriptional initiation regions (promoter regions), either constitutive or inducible, may be employed. The transcriptional initiation region is joined to the structural gene(s) encoding the agarase activity to provide for transcriptional initiation upstream from the initiation codon, normally within about 200 bases of the initiation codon, where the untranslated 5'-region lacks an ATG. The 3'-end of the structural gene will have one or more stop codons which will be joined to a transcriptional termination region functional in a bacterial host, which termination region may be associated with the same or a different structural gene as the initiation region.

The expression cassette is characterized by having the initiation region, the structural gene under the transcriptional control of the initiation region, and the termination region providing for termination of transcription and processing of the messenger RNA in the direction of transcription as appropriate.

The various sequences may be joined together in conventional ways. The sequences may be cloned and joined in the proper orientation to provide for constitutive expression of the agarase gene in a selected host.

Formulations of the purified agarase enzyme system could include other additives, such as detergents, adjuvants, spreading agents, sticking agents, stabilizing agents, or the like. The formulations may either be wet or dry preparations, including flowable powders, emulsifiable concentrates and liquid concentrates, such as are known in the art. The agarase preparations may be applied in accordance with conventional methods. Suitable methods for applying may include spraying, painting, coating, immersing and the like.

The following is further exemplary of the invention, and specifically defines preferred techniques for the purification of an agarase enzyme system, isolation of the gene(s) coding for the agarase enzyme system, and assay methods for defining and characterizing the agarase enzyme system having a high degree of agarase activity.

The following examples are offered by way of illustration and not by way of limitation.

THE EXAMPLES

The examples disclose a novel agarase enzyme system, and the gene(s) coding therefor, which were isolated from the purified, isolated bacterial strain 2-40 (ATCC No. 43961). Utilizing the suicide vector pEcoR252, the 2-40 agarase gene(s) were cloned and expressed in *E. coli* HB101, allowing the *E. coli* to utilize agarose as the sole carbon source. Furthermore, the cellular distribution, substrate specificity and end products of the 2-40 agarase system have been identified and characterized by means of a novel assay method comprising a ferric cyanide reducing sugar assay in conjunction with thin layer chromotography.

Restriction enzymes, ligase, and all commercially available reagents were utilized according to manufacturer's recommendations. Standard methods in cloning and molecular analysis were performed according to Sambrook, Fritsch and Maniatis, 1989. *Molecular Cloning: A Laboratory Manual*, 2nd Ed., Cold Spring Harbor Laboratory, New York (hereinafter Maniatis).

EXAMPLE 1

PURIFICATION OF THE 2-40 AGARASE ENZYME SYSTEM USING THE AGARASE ACTIVITY GEL TECHNIQUE

A culture flask with 10 ml of 2-40 minimal media was inoculated with a loopful of bacterial strain 2-40 and grown overnight at 20° C. with shaking at 200 RPM. [2-40 minimal agarase induction media: 6.9 g sea salts; 0.3 g yeast extract; 0.6 g agarose (IBI electrophoresis grade); 283 ml distilled water ($dH_2O$); autoclaved and cooled to 55° C.; followed by the addition of 15 ml 1M Tris pH 7.6 (50 mM final concentration) and 1.5 ml $NH_4Cl$ (1.87M; 0.5 g/1 final concentration)]. The following day, 6 ml of the overnight culture was innoculated into 300 ml of fresh 2-40 minimal media. The cells were grown at 25° C., with shaking at 200 RPM for 30 hours. See, FIG. 3 and FIG. 4.

At 30 hours, the cells were harvested by centrifugation at 7,000 RPM for 15 minutes at 4° C. The supernatant was removed to a new tube and filtered through an Amicon centriprep tube with a 30,000 MW cut off. The agarase activities were retained in the concentrated fraction having a molecular weight over 30,000. A buffer exchange was also done at this point by adding about 10 ml of 20 mM Pipes buffer, pH 6.8 and filtering through the apparatus as was done with the supernatant.

The concentrated retentate over 30,000 MW is then fractionated on a non-denaturing polyacrylamide protein separation gel. The 7% polyacrylamide gel was prepared following standard procedures under non-denaturing conditions and electrophoresed in the standard manner of a protein separation gel, except that is, it was allowed to run until the dye front is just to the bottom of the gel.

Following electrophoresis, the 7% separation gel was removed to a shallow glass dish to which 20 mM Pipes buffer, pH 6.8, was added to barely cover the gel. Then, an unused 7% acrylamide gel (1.5 mm thick; 0.1% final concentration of agarose) was laid directly on top of the separation gel which had been placed in the glass dish. The dish was covered with plastic wrap and placed so that nothing would dislodge the overlay or disrupt its orientation with the gel beneath it during 48 hours of incubation at 45° C. Pipes buffer was added as necessary to keep the two gels moist during the incubation.

At the end of the 48-hour incubation period, the overlay gel was removed and rinsed with room temperature $dH_2O$. The overlay gel was then placed into another glass dish containing the iodine stain (0.12 M KI and 0.5 M I in $dH_2O$) and allowed to soak. The staining reaction was intensified when the gel was refrigerated. An unstained region indicated agarase activity and it also indicates where the protein bands are.

A comparison of the activity bands with the placement of pre-stained high molecular weight protein standards was used to determine the point at which each active fragment of the agarase enzyme would migrate on a standard separation gel. A second protein separation gel was subsequently run and the appropriate areas of active regions on the gel were excised by refering to adjacent lanes of pre-stained high molecular weight protein standards. Finally, the purified agarase was electroeluted from the gel slices by the method of Maniatis.

EXAMPLE 2

ALTERNATIVE PURIFICATION METHOD

A. Gel Permeation Chromatography

The concentrated fraction having a molecular weight over 30,000 MW, separated as above by an Amicon centriprep tube, was passed through a Sephacryl S-200 (Pharmacia) size exclusion column matrix. Each eluted fraction was assayed for agarase activity using the ferric cyanide reducing sugar assay.

In order to prepare for the ferric cyanide reducing sugar assay, the following were placed into an Eppendorf tube with 100 µl of the enzyme preparation: 200 µl 20 mM Pipes buffer, pH 6.8; 100 µl substrate (agarose, neoagarotetraose, and/or neoagarobiose to a final concentration of 0.2%). The mixture was reacted overnight at 45° C. Then, the ferric cyanide reducing sugar assay was performed on the reacted mixture as follows: 200 µl Stop Reagent (1% w/v $Na_2HPO_4 7H_2O$, 1% w/v NaOH) and 300 µl Color Reagent (0.116% w/v $K_3[Fe(CN)_6]$, 0.22% w/v NaOH) were added to the reaction mixture, then boiled 3.5 minutes, cooled to room temperature and the optical density absorbance at 420 nm determined. The measurements for the experimental preparation were compared to a glucose standard curve (0–100 g/ml glucose concentrations) to evaluate the reducing sugar equivalents.

Those fractions which showed positive agarase activity were loaded onto a protein separating gel as described above to ascertain that only one protein was present in the fraction. When more than one protein was present, the activity gel method described above can be used to further separate and to identify the agarase.

B. Affinity Chromatography

It was known that at least one of the B-agarases of strain 2-40 binds very strongly with agarose. Therefore, a disposable 20 ml column (BioRad) was packed with (BioRad) Bio-Gel A-50 m beads which include agarose as one of their components. The concentrated agarase fraction having a molecular weight over 30,000, separated as above by an Amicon centriprep tube, was loaded onto the column and allowed to flow through by gravity.

The agarase was bound to the beads, while other proteins were flushed through the column. The purified agarase was then eluted from the column by increasing the pH of the Pipes buffer eluant and/or by altering the osmolarity.

EXAMPLE 3

PROCEDURES FOR PREPARING AND SCREENING THE 2-40 GENE BANK IN VECTOR pEcoR252

Purified 2-40 chromosomal DNA was partially digested with Sau 3A and fragments ranging in size from about 8 to 10 kb were selected. The fragments were selected for the size corresponding to the agarase enzyme system gene(s). The suicide vector pEcoR252 was digested with Bgl II. Then, the linearized vector fragments and the Sau 3A fragments of insert DNA were combined at a 2:1 molar ratio (vector:insert) to produce a final concentration of 2.5 pmoles DNA in a 20 µl reaction volume. The fragments were ligated overnight at 15° C., purified and quantitated. Meanwhile, competent *E. coli* HB101 host cells were prepared, and subsequently transformed by the pEcoR252 vector into which the Sau 3A DNA fragments had been ligated according to standard procedures. DNA gene pools were prepared from the transformed host cells and used to re-transform competent *E. coli* HB101 with DNA pools. Finally, the transformed host cells were screened for agarase clones.

A. Sau 3A Partial Digest of 2-40 Genomic DNA

Chromosomal DNA was purified from bacterial strain 2-40, according to the methods of Maniatis. Then, the extracted 2-40 chromosomal DNA was partially digested by the Sau 3A restriction endonuclease. In the partial digestion, 1.5 units of Sau 3A (1 µl) were added to 50 g 2-40 chromosomal DNA (1.5 g/ml; 33.33 µl used) in 10× High Restriction Enzyme Buffer (4 µl) with $dH_2O$ (1.67 µl). The Sau 3A restriction enzyme digestion was permitted to procede at 37° C. for 18 minutes, and then the enzyme was heat inactivated at 65° C. for 10 minutes.

A 0.7% agarose gel was loaded with 1 g of the Sau 3A partially digested DNA and electrophoretically size fractionated. The completed gel was compared to n/Hind III standards to determine the degree of Sau 3A digestion. When the degree of digestion was sufficient, the remaining 2-40 DNA Sau 3A partially digested DNA was electrophoretically size selected on another 0.7% agarose gel. The resulting smear of randomly sized 2-40 DNA fragments on the gel was excised as thin gel slices in the molecular weight range equivalent to about 8 kilobases (kb). Finally, the size selected 2-40 genomic DNA 8 kb fragments were electroeluted from each gel slice and quantitated according to the methods of Maniatis.

B. Preparation of the DEcoR252 Vector

Since pEcoR252 must be grown in a λ lysogenic strain of *E. coli*, strain K514λ was used as the host cell. K514λ was made competent in the standard manner of Maniatis, then tranformed with pEcoR252 DNA, briefly describes as follows:

1) 30 g pEcoR252 DNA was placed in a sterile microfuge tube with 100 µl competent K514λ and mixed well by pipette;
2) incubated on ice 30 minutes;
3) incubated at 42° C. for 5 minutes;
4) 1 ml Luria broth (sterile) was added to the tube and incubated at 37° C. for 40 minutes to allow time for expression of ampicillin resistance; and
5) 100 µl were plated onto Luria agar plates with ampicillin (100 g/ml) and incubated overnight at 30° C.

The same methods were used to develop a corresponding control, except pEcoR252 DNA was not added to the competent cells. The competency level was determined by plating 200 µl onto one Luria agar plate with ampicillin (100 µg/ml) and a dilution series $10^{-5}$ to $10^{-7}$ on the remaining Luria agar plates with ampicillin (100 g/ml). As an additional control, the same methods were used with pBR322, and then $10^{-1}$ to $10^{-4}$ dilutions were plated onto Luria agar plates with ampicillin (100 g/ml).

C. Bgl II Digestion of pEcoR252

Plasmid DNA was purified from the K514A culture, which had been transformed with pEcoR252, according to the methods of Maniatis. Then, the purified plasmid DNA was digested with the restriction endonuclease, Bgl II. In the restriction digest, 5 units of Bgl II (1 µl) were added to 0.5 g pEcoR252 DNA (25 µl) in 10× High Restriction Enzyme Buffer (3 µl) with dH$_2$O (1 µl). The Bgl II restriction enzyme digestion was permitted to procede at 37° C. for 1 hour, and then the enzyme was heat inactivated to stop the enzyme reaction. The cut plasmid DNA was precipitated from solution overnight in 2 volumes of ethanol, then microfuged and the supernatants discarded. The DNA cell pellets were washed with 70% ethanol, dried in a Speed-vac for 5 minutes, resuspended in 1× TE (Tris, EDTA) buffer, and then quantitated according to the methods of Maniatis.

D. Ligation and Ligated DNA Purification

Ligations were performed at a 2:1 molar ratio of vector:insert DNA at a final concentration of 2.5 pM/ml in 2.0 µl total volume. The determination of the DNA molar ratios was calculated as follows: 1 pM=molecular weight of DNA expressed in µg.

|  | 1 pM | 0.05 pM | 2:1 ratio |
| --- | --- | --- | --- |
| 2-40 genome DNA 8 Kb × .662 = | 5.30 | 0.26 µg × | ½ 0.0882 µg |
| PEcoR252 vector DNA 3.32 kb × .662 = | 2.2 µg | 0.11 µg × | ½ 0.0733 µg |

Thus, since the concentration of vector pEcoR252 was 10 ng/µl, 7.3 µl were used, and since the concentration of 8 kb genomic 2-40 DNA was 12 ng/µl, 7.35 µl were used.

The ligation reaction was performed on ice as follows: 7.3 µl Bgl II cut pEcoR252 (0.0733 µg) was mixed with 7.35 µl 18 kb Sau 3A fragment of 2-40 genomic DNA (0.088 g), 1.0 µl ligase (0.1 unit ligase in storage buffer) was added with 4.0 µl 5× ligation buffer (final 1× concentration). The ligation reaction was run overnight at 15° C. [5× Ligation Buffer: 7.5 µl 1M Tris pH 7.6; 2.5 µl 1M MgCl$_2$; 2.5 µl 1M DTT; 1.25 µl 100 mM ATP; 25 µl 1 mg/ml acetylated BSA; 11.25 µl dH$_2$O].

The ligated DNA was purified as follows: 30 µl dHO was added to the ligation reaction (50 µl final volume). The ligated DNA was phenol/chloroform extracted and ammonium acetate (7.5M) precipitated according to standard methods. The tube was microfuged 15 minutes and the supernatant removed to new tube, washed with approximately 1 ml 70% ethanol, then microfuged to pellet the DNA. The ethanol was discarded and the DNA pellet was dried in a Speed-vac, then resuspended in 20 µl TE buffer.

E. Transformation of E. coli HB101

Figure 2:
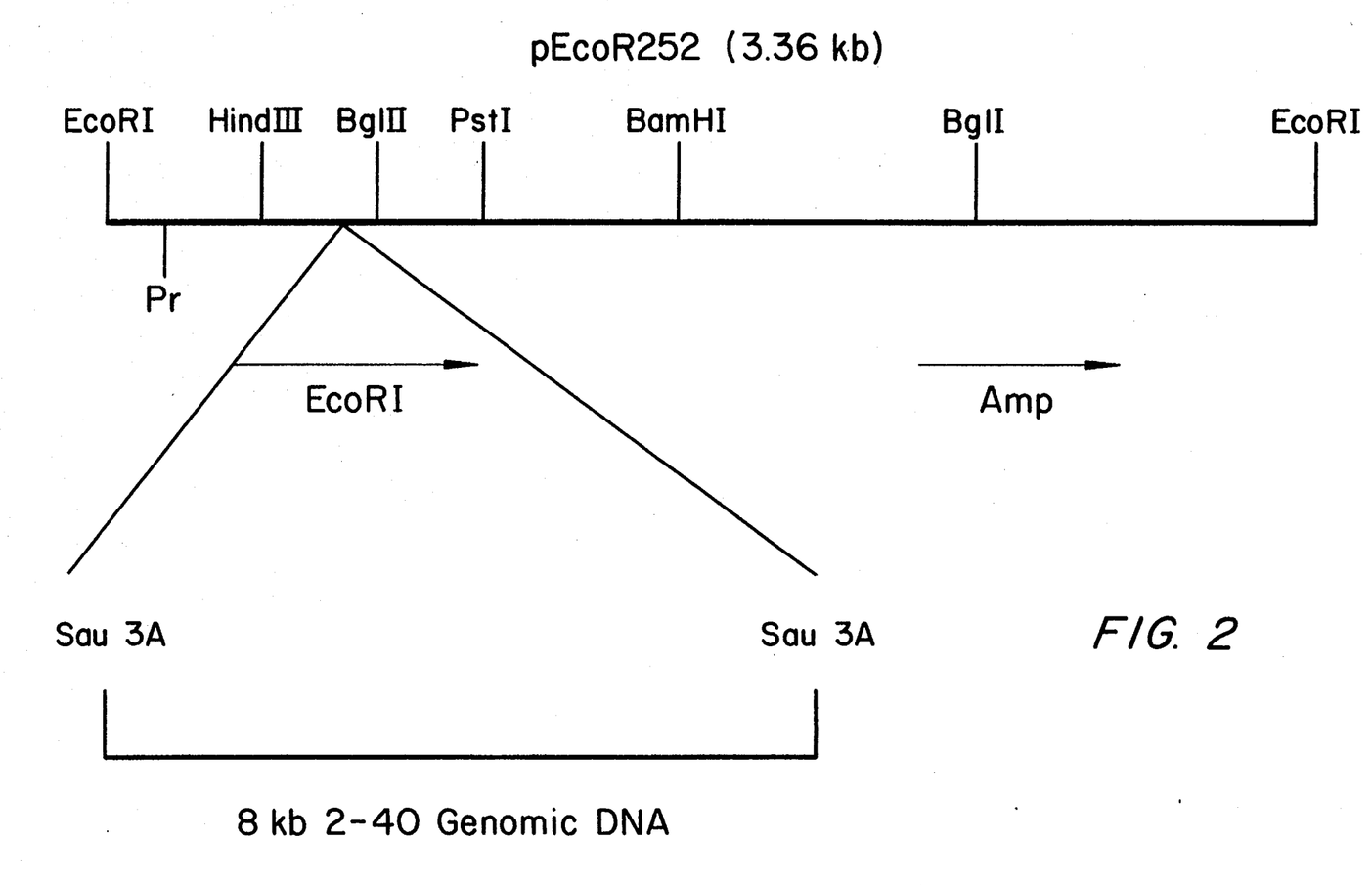
FIG. 2 is a diagramatic representation of the construct of the agarase enzyme gene(s) in the pEcoR252 expression vector.

An aliquot of approximately 30 g purified ligated DNA (FIG. 2) was placed in each of 5 sterile microfuge tubes with 100 µl thoroughly suspended E. coli HB101 competent cells, and gently mixed by pipette. The tubes were incubated on ice for 30 minutes, and then incubated at 42° C. for 5 minutes. Then, 1 ml Luria broth was added to each tube and incubated at 42° C. for 30 minutes to allow expression of ampicillin resistance.

Following incubation, the tubes were vortexed to resuspend the contents and the 5 transformation mixes were pooled into 95 ml Luria broth (prewarmed to 42° C.) containing 100 µg/ml ampicillin in a 500 ml flask. The pooled transformation mix was shaken thoroughly at 42° C. for 1 hour to kill parentals. The transformed cells were centrifuged at 5000 RPM for 5 minutes in a sterile GSA tube, the supernatant was removed, and then the cell pellet was completely resuspended in 1 ml Luria broth.

The transformed cells were plated (100 µl cells/plate) by spreading with a glass spreader onto Luria agar plates with 100 µg/ml ampicillin, then incubated overnight at 30° C.

Corresponding controls were made utilizing:
a) 100 µl competent cells only;
b) 50 ng pBR322 with 100 µl competent cells; and
c) 30 ng uncut pEcoR252 with 100 µl competent cells.

Each control was incubated for 30 minutes on ice, then 5 minutes at 42° C. Next, 1 ml Luria broth was added to each control and the tubes were incubated at 42° C. for 30 minutes.

Following incubation, each control was added to a separate 150 ml flask containing 19 ml Luria broth (prewarmed to 42C) containing 100 µg/ml ampicillin. Immediately, each control was plated (200 µl cells/plate) by spreading with glass spreader onto Luria agar plates with 100 µg/ml ampicillin. The remaining cultures were shaken thoroughly at 42° C. for 1 hour, then 200 µl of each control was plated (200 µl cells/plate) by spreading with glass spreader onto Luria agar plates with 100 µg/ml ampicillin, then incubated overnight at 37° C.

F. Preparation of DNA Pools from the Gene Bank (pEcoR252)

Each cell culture plate was flooded with 1 ml Luria broth and swirled to dislodge colonies. Then, each cell suspension was transfered by pipette to individual Eppendorf tubes. The procedure was repeated, and each plate was again washed with a second aliquot of 1 ml Luria broth, which was subsequently added to the Eppendorf tube. Each Eppendorf was microfuged for 2 minutes to pellet the cells, then the supernatant was removed.

The DNA was extracted from the cells by the alkaline lysis method for plasmid purification as describe in Maniatis. The cell pellet was suspended in 100 µl of Solution 1 and permitted to stand at room temperature for 5 minutes. Then, 200 µl fresh lysing Solution 2 was added to each and the tubes were placed on ice for 10 minutes. Finally, 150 µl precooled Solution 3 was added to each tube and vortexed in the inverted position for 10 seconds, then the tubes were placed on ice for 20 minutes.

The tubes were microfuged to effectively pellet the cellular debris, and the DNA-containing supernatant of each was transfered to a fresh Eppendorf tube. The DNA in each tube was purified by precipitation overnight at room temperature after mixing with 1 µl of 1 mg/ml yeast RNA in 2× volumes 100% ethanol. Then, the tubes were microfuged for 15 minutes to precipitate the DNA, after which the supernatants were discarded. The DNA cell pellets were washed with 70% ethanol, dried in a Speed-vac for 5 minutes, and resuspended in 250 µl TE buffer. Finally, the DNA in each tube was again precipitated by adding 125 µl 7.5M ammonium acetate and standing at room temperature for 1 hour. Each tube was microfuged for 15 minutes, and the supernatant was transfered to fresh Eppendorf tubes. The DNA was precipitated in 750 μl 100% ethanol with standing overnight at room temperature. As above, each tube was microfuged for 15 minutes, after which the supernatants were discarded, then the DNA cell pellets were washed with 70% ethanol, dried in a Speed-vac for 5 minutes, and resuspended in 250 μl TE buffer. The 15 DNA pools were quantitated by electrophoresing 8 μl of a 1/10 dilution of each sample on a 1% agarose gel and comparing to A standards.

G. Screening the DNA Gene Pools for Agarase

HB101 competent cells were transformed with the 2-40 Gene Bank DNA pools, essentially following the methods set forth in Example 3, section E, in order to select for agarases. An aliquot of 20 g from each of the 15 DNA pools, representing the 2-40 DNA gene bank, were placed in sterile microfuge tubes to which 100 μl competent E. coli HB101 were added and mixed by gentle pipetting. The mixture was incubated on ice for ½ hour, then incubated at 42° C. for 5 minutes. Then, 1 ml Luria broth was added to each tube and incubated at 42° C. for ½ hour to allow expression of the ampicillin resistance.

The entire contents of each Eppendorf tube (1.1 ml) were plated onto selective media (100 μl/plate or about 11 plates/gene pool). The selective media was prepared as follows: $Na_2HPO_4$ (6 g), $KH_2PO_4$ (3 g), and NaCl (0.5 g) were mixed in 950 ml dHO, adjusted to pH 7.4, and then 20 g agar was added (2% final concentration). The solution was autoclaved and cooled to 55° C. Then the following sterile components were added: 10% urea stock (10 ml); 25 mg/ml ampicillin (2 ml; 500 g/ml final); 1M $MgSo_4$ (2 ml); 1M $CaCl_2$ (0.1 ml); thiamine (125 μl of a 4 mg/ml stock; 0.5 mg/l final); L-proline (1 ml of a 40 mg/ml stock; 40 μg/ml final); and L-leucine (5 ml of a 8 mg/ml stock; 40 g/ml final).

The inoculated plates were incubated at 37° C. for 24 hours, then at 30° C. for 24 hours, and then at room temperature until colonies appeared (up to 5 days). The plates were then held at 30° C. for an additional 24 hours, then stored at room temperature. The only colonies which can grow, on the specifically prepared selective media, utilize agar as the sole carbon source; therefore, the colonies represent 2-40 DNA transformed E. coli agarase clones.

The selectively cultured colonies were replated and incubated until colonies appeared. Then, the plates were flooded with the iodine assay solution (0.12M KI and 0.5M I in $dH_2O$). Cleared zones around a colony specifically indicated agarase activity.

Deposits of the transformed *Escherichia coli* HB101, designated p5-2, which was transformed by the expression vector plasmid pEcoR252 containing the gene(s) coding for the agarase enzyme system derived from the 2-40 gene bank (ATCC No. 68582) have been made with the American Type Culture Collection at 12301 Parklawn Drive, Rockville, Maryland 20852, on April 15, 1991. The specimen, on patenting will be maintained on deposit for a period of thirty years, for five years after the last request for a specimen, or for the enforceable life of the patent, whichever is longer. Should the deposits become nonviable they will be replaced. Assurance of access to the deposit as determined by the Commissioner under 37 C.F.R. 1.14 which provides for restrictions on the availability of the deposit to the public will be irrevocably removed on the granting of a patent.

Although the foregoing invention has been described in some detail by way of illustration and example for purposes of clarity and understanding, it will be obvious that certain changes and modifications may be practiced within the scope of the appended claims without departing from the spirit and scope of the invention.

What is claimed is:

1. An isolated and purified agarase enzyme system which can digest agarose into its component monosaccharides isolated from bacterial strain 2-40 by a method comprising;
   a) amplifying the cells of strain 2-40 on minimal media supplemented with an agar or agarase carbon source;
   b) harvesting the cell supernatant;
   c) selecting the cell supernatant for molecular weight fragments greater than 30,000;
   d) electrophoretically size fractionating the selected portion of the cell supernatant on a separation polyacrylamide gel;
   e) blotting the gel containing the size fractionated supernatant of step (d) in direct contact with an overlay second polyacrylamide gel;
   f) visualizing the agarase activity on the overlay gel by means of an iodine staining assay;
   g) excising the agarase active regions from a third polyacrylamide gel used to electrophoretically fractionate the 2-40 cell supernatant by the manner of steps (b) through (d); and
   h) electroeluting agarase of high specific activity from the excised agarase active regions of step (g).

2. The agarase enzyme system of claim 1, wherein said enzyme system is capable of depolymerization of complex polysaccharides.

3. An isolated and purified agarase enzyme system which can degrade agarose into its component monosaccharides which results from the expression of a DNA sequence from bacterial strain 2-40 encoding said agarase enzyme system inserted into plasmid pEcoR252.

4. The agarase enzyme system of claim 3, wherein agarase enzyme system is capable of depolymerizing complex carbohydrates.

5. The agarase enzyme system of claim 4, wherein said complex carbohydrate is agar, agarose, alginic acid, carboxymethyl cellulose, chitin, glycogen, laminafin, pullulan, sodium polygalacturonate starch, or xylan.

6. The agarase enzyme system of claim 5, wherein said complex carbohydrate is agar or agarose.

7. An isolated and purified agarase enzyme system which can digest agarose into its component monosaccharides, isolated from bacterial strain 2-40.

* * * * *